United States Patent [19]

Schirmer et al.

[11] 4,405,358
[45] Sep. 20, 1983

[54] ARALKYLANILINE DERIVATIVES, AND HERBICIDES WHICH CONTAIN THESE COMPOUNDS

[75] Inventors: Ulrich Schirmer, Heidelberg; Wolfgang Rohr, Wachenheim; Bruno Wuerzer, Otterstadt, all of Fed. Rep. of Germany

[73] Assignee: BASF Aktiengesellschaft, Fed. Rep. of Germany

[21] Appl. No.: 259,618

[22] Filed: May 1, 1981

[30] Foreign Application Priority Data

May 31, 1980 [DE] Fed. Rep. of Germany ....... 3020784

[51] Int. Cl.³ .................... A01N 9/12; A01N 9/14; A01N 9/16; A01N 9/20; C07C 103/34; C07C 69/76
[52] U.S. Cl. ...................... 71/98; 564/221; 71/100; 564/222; 71/103; 71/104; 71/105; 71/106; 71/111; 71/114; 71/118; 71/120; 260/456 A; 260/465 D; 560/9; 560/12; 560/27; 562/426; 562/430; 562/439; 562/441; 562/455; 562/456; 562/457; 564/49; 564/50; 564/85; 564/86; 564/123; 564/154; 564/155; 564/190; 564/202; 564/207; 564/211
[58] Field of Search ............... 564/202, 207, 211, 221, 564/222, 49, 50, 154, 155, 86, 85, 123, 190; 260/465 D, 456 A; 560/27, 9, 12; 71/100, 105, 106, 111, 118, 114, 98, 120, 104, 103; 562/426, 430, 439, 441, 455, 456, 457

[56] References Cited

U.S. PATENT DOCUMENTS

| 2,511,028 | 6/1950 | Whitman | 564/221 X |
| 3,567,765 | 3/1971 | Thiele | 564/221 X |
| 3,839,447 | 10/1974 | Swiger et al. | 564/207 X |
| 4,181,519 | 1/1980 | Pilgram et al. | 71/118 X |
| 4,204,858 | 5/1980 | Baker | 71/111 |

FOREIGN PATENT DOCUMENTS

| 749581 | 10/1970 | Belgium | 71/118 |
| 2855699 | 6/1979 | Fed. Rep. of Germany . | |
| 47-38033 | 4/1972 | Japan | 71/111 |
| 55-148 | 4/1980 | Japan | 71/118 |

OTHER PUBLICATIONS

Mann et al., CA 49: 13136c, (1955).
Schmutz et al., CA 62: 14682c, (1965).
Schmidt et al., Chem. Ber. 105, 1634–1637, (1972).

Primary Examiner—Thomas A. Waltz
Attorney, Agent, or Firm—Keil & Witherspoon

[57] ABSTRACT

Aralkyaniline derivatives of the general formula

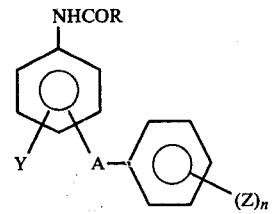

where R is alkoxy, cycloalkoxy, alkenyloxy, alkynyloxy, cyanoalkoxy, haloalkoxy, alkylthio, alkenylthio or alkynylthio or unsubstituted or substituted alkyl, cycloalkyl, alkenyl or alkynyl, Y is hydrogen, alkyl, halogen, alkoxy or haloalkyl, A is unsubstituted or substituted alkylene, Z is hydrogen, alkyl, haloalkyl, alkoxyalkyl, cycloalkyl, aralkyl, aryl, aryloxy, halogen, a $C_4H_4$-chain which is fused to the benzene radical to form an unsubstituted or substituted naphthyl radical, alkoxy, haloalkoxy, alkylthio, thiocyanato, cyano,

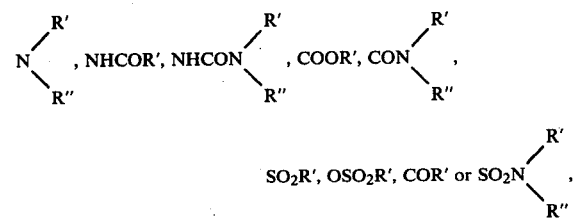

$R'$ and $R''$ each, independently of one another, being hydrogen, alkyl, alkoxy, alkylthio, cycloalkyl or unsubstituted or substituted phenyl, and n is an integer from 1 to 4, and herbicides containing these compounds.

3 Claims, No Drawings

ARALKYLANILINE DERIVATIVES, AND HERBICIDES WHICH CONTAIN THESE COMPOUNDS

The present invention relates to novel aralkylaniline derivatives and to herbicides which contain these compounds.

German Laid-Open Application DOS No. 2,855,699 discloses that aralkoxyaniline derivatives have a herbicidal action.

We have found that aralkylaniline derivatives of the formula

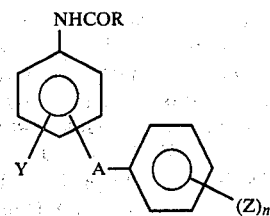

where R is alkoxy, cycloalkoxy, alkenyloxy, alkynyloxy, cyanoalkoxy, haloalkoxy, alkylthio, alkenylthio or alkynylthio or unsubstituted or halogen-, alkoxy-, alkoxycarbonyl- or cyano-substituted alkyl, cycloalkyl, alkenyl or alkynyl, Y is hydrogen, alkyl, halogen, alkoxy or haloalkyl, A is unsubstituted or alkyl-substituted alkylene, Z is hydrogen, alkyl, haloalkyl, alkoxyalkyl, cycloalkyl, aralkyl, aryl, aryloxy, halogen, a C$_4$H$_4$-chain which is fused to the benzene radical to form an unsubstituted or substituted naphthyl radical, alkoxy, haloalkoxy, alkylthio, thiocyanato, cyano,

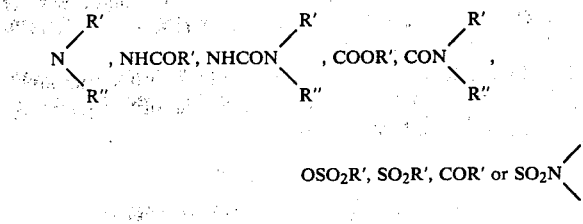

R' and R" each, independently of one another, being hydrogen, alkyl, alkoxy, alkylthio, cycloalkyl or unsubstituted or alkyl-, halogen- or alkoxy-substituted phenyl, and n is an integer from 1 to 4, exhibit an improved herbicidal action in respect of numerous important undesired plants and are tolerated by various crop plants.

The radicals shown in the general formula can, for example, have the following meanings:

R can be unsubstituted or halogen-, alkoxy-, alkoxycarbonyl- or cyano-substituted alkyl, cycloalkyl, alkenyl or alkynyl (eg. methyl, ethyl, isopropyl, n-propyl, n-butyl, sec.-butyl, tert.-butyl, iso-butyl, sec.-pentyl, chloromethyl, α,α-dichloroethyl, dichloromethyl, methoxymethyl, acetoxymethyl, cyanomethyl, cyclopropyl, cyclohexyl, α-methylcyclopropyl, sec.-propenyl or ethynyl), or alkoxy (eg. methoxy, ethoxy, n-propoxy, iso-propoxy, tert.-butoxy or sec.-butoxy), cycloalkoxy (eg. cyclohexoxy), alkenyloxy (eg. propenoxy), alkynyloxy (eg. sec.-butynoxy), cyanoalkoxy (eg. 2-cyanoethoxy), haloalkoxy (eg. chloromethoxy), alkylthio (eg. methylthio, ethylthio, n-propylthio or t.-butylthio), alkenylthio or alkynylthio; Y can be hydrogen, alkyl (eg. methyl or t.-butyl), halogen (eg. fluorine, chlorine or bromine), alkoxy (eg. methoxy) or haloalkyl (eg. trifluoromethyl); A can be unsubstituted or alkyl-substituted alkylene, for example of 1 to 10 carbon atoms (eg. methylene, methylmethylene, dimethylmethylene, propylene, hexylene, ethylene, methylethylene, methylpropylene, ethylpropylene, butylene, pentylene, methylpentylene, dimethylpropylene, heptylene, ethylbutylene or trimethylpentylene); Z can be hydrogen, alkyl (eg. methyl, ethyl or t.-butyl), haloalkyl (eg. trifluoromethyl), alkoxyalkyl (eg. methoxymethyl), cycloalkyl (eg. cyclohexyl), aralkyl (eg. benzyl), aryl (eg. phenyl), aryloxy (eg. phenoxy), halogen (eg. fluorine, chlorine, bromine or iodine), a C$_4$H$_4$-chain, which is fused to the benzene ring to form an unsubstituted or substituted naphthyl ring, alkoxy (eg. isopropoxy or hexoxy), haloalkoxy (eg. 1,1,2,2-tetrafluoroethoxy), alkylthio (eg. methylthio), thiocyanato, cyano,

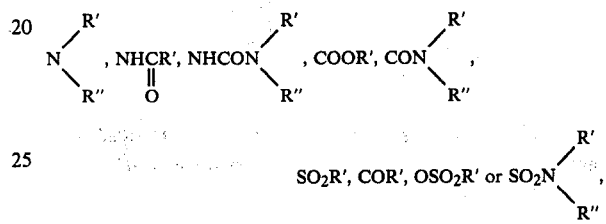

and R' and R" can each, independently of one another, be hydrogen, alkyl (eg. methyl or ethyl), alkoxy (eg. methoxy or tert.-butoxy), alkylthio (eg. methylthio), cycloalkyl (eg. cyclohexyl) or unsubstituted or alkyl-, halogen- or alkoxy-substituted phenyl (eg. phenyl, 3-chlorophenyl, 4-methylphenyl or 3-methoxyphenyl).

The novel compounds can, for example, be prepared by the following processes:

PROCESS I

An aralkylphenyl isocyanate of the formula

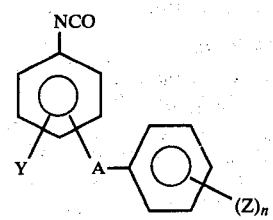

where Y, A and (Z)$_n$ have the above meanings, is reacted with a compound of the formula RH, for example an alkanol, cycloalkanol, alkenol, alkynol, cyanoalkanol, haloalkanol, alkylmercaptan, alkenylmercaptan or alkynylmercaptan.

The reaction is carried out in the presence or absence of a conventional catalyst for isocyanate reactions, for example a tertiary amine (triethylamine or 1,4-diazabicyclo-(2,2,2)-octane), a nitrogen-containing heterocyclic compound (pyridine or 1,2-dimethylimidazole) or an organic tin compound (dibutyl-tin diacetate or dimethyl-tin dichloride), and in the presence or absence of a solvent which is inert under the reaction conditions, for example a hydrocarbon (naphtha, gasoline, toluene, pentane or cyclohexane), a halohydrocarbon (methylene chloride, chloroform, dichloroethane, chlorobenzene or o-, m- or p-dichlorobenzene), a nitrohydrocarbon (nitrobenzene or nitromethane), a nitrile (acetonitrile, butyronitrile or benzonitrile), an ether (diethyl ether, tetrahydrofuran or dioxane), an ester (ethyl acetate or methyl propionate), a ketone (acetone or methyl ethyl ketone) or an amide (dimethylformamide or formamide), at from 0° to 150° C., preferably from 40° to 100° C. (cf. S. Petersen in Methoden der Organ. Chemie, Volume VIII, page 131, Georg-Thieme-Verlag, Stuttgart, 4th edition (1952)).

PROCESS II

An aralkylaniline of the formula

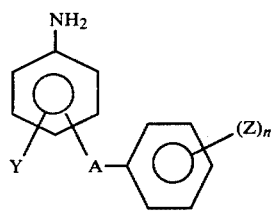

where Y, A and (Z)$_n$ have the above meanings, is reacted with a compound of the general formula

where X is a leaving group (eg. chlorine, bromine or

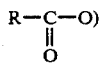

and R has the above meanings, in a suitable solvent, for example water, an alcohol (methanol, ethanol or isopropanol) or one of those mentioned for process I, in the presence of a conventional acid acceptor, for example an alkali metal hydroxide, carbonate or bicarbonate, alkaline earth metal oxide, hydroxide, carbonate or bicarbonate, or tertiary organic base (eg. triethylamine, pyridine, N,N-dimethylaniline, N,N-dimethylcyclohexylamine, quinoline or tributylamine), at from −20° to 150° C., preferably from 20° to 80° C. (cf. German Laid-Open Application DOS No. 1,643,763).

PROCESS III

A nitrobenzene of the general formula

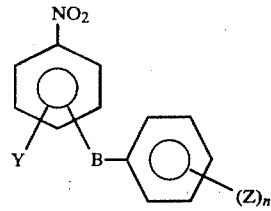

where B is a saturated or unsaturated unsubstituted or alkyl-substituted alkylene chain, which can be interrupted by a keto group, or B is a keto group, and Y and (Z)$_n$ have the above meanings, is hydrogenated in the presence of an acid anhydride of the general formula

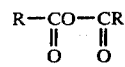

where R has the above meanings, in a suitable solvent, for example an alkanoic acid

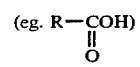

or an ether (eg. tetrahydrofuran (THF)), in the presence of a hydrogenation catalyst (eg. palladium-on-charcoal, platinum sponge or Raney nickel), at from 20° to 150° C., under atmospheric or superatmospheric pressure.

To prepare the aralkylphenyl isocyanate required for process I, an aralkylaniline of the formula shown in connection with process II is reacted with phosgene in a conventional manner (W. Siefken, J. Liebigs Annalen der Chemie 562 (1949), 75 et seq.). To prepare the aralkylaniline required in process II, a nitrobenzene of the formula shown in connection with process III is hydrogenated catalytically, in the presence of a conventional hydrogenation catalyst (eg. palladium-on-charcoal, platinum sponge or Raney nickel), a suitable solvent, such as a carboxylic acid (eg. acetic acid), an ether (eg. THF) or an alcohol (eg. ethanol) and, where appropriate, a strong acid (eg. methanesulfonic acid or sulfuric acid), at from 0° to 150° C., under a pressure of from 1 to 100 bar. (B. R. Baker et al., J. Pharm. Sci. 56 (1967), 737-742).

The requisite nitrobenzenes can be prepared by conventional methods (cf. B. R. Baker et al., J. Pharm. Sci. 56 (1967), 737-742; P. Pfeiffer et al., J. Prakt. Chem. 109 (1925), 41; R. Geigy and W. Koenigs, Chem. Ber. 18 (1885), 2401-2407; P. Petrenko-Kritschenko, Chem. Ber. 25 (1892), 2239-2242).

The Examples and methods which follow illustrate the preparation of the novel aralkylaniline derivatives and of their intermediates.

METHOD A 3-(3-Phenylpropyl)-phenyl isocyanate 170 g of phosgene are dissolved in 200 ml of toluene at −10° C. 145 g of 3-(3-phenylpropyl)-aniline, dissolved in 300 ml of toluene, are slowly added dropwise at −10° C. The mixture is warmed slowly, phosgene is introduced at 60° C., and the mixture is brought to the boil. After 6 hours, excess phosgene is flushed out with nitrogen and the mixture is distilled. 156 g of 3-(3-phenylpropyl)-phenyl isocyanate, of boiling point 107°-110° C./0.1 mbar, are obtained.

METHOD B 3-(3-Phenylpropyl)-aniline 253 g of 1-phenyl-3-(3'-nitrophenyl)-prop-2-en-1-one are suspended in 2.5 liters of glacial acetic acid. 196 g of concentrated sulfuric acid and 10 g of 10% strength Pd on animal charcoal are added and the mixture is hydrogenated under 1.1 bar hydrogen pressure, at 65°-70° C., until hydrogen is no longer absorbed. When the mixture has cooled, part of the acetic acid is distilled off, the residue is rendered alkaline with sodium hydroxide solution and extracted with ether, the organic phase is dried with sodium sulfate and filtered, the solvent is distilled off and the residue is then distilled. 150 g of 3-(3-phenylpropyl)-aniline, of boiling point 148° C./0.2 mbar, are obtained.

The following aralkylanilines can be prepared by similar methods: 3-benzylaniline (melting point 43°–45° C.), 3-(3-(2-chlorophenyl)-propyl)-aniline (boiling point 156°–158° C./0.1 mm Hg), 3-(3-(4-chlorophenyl)-propyl)-aniline (boiling point 160°–161° C./0.1 mm Hg), 3-(3-(2-methoxyphenyl)-propyl)-aniline (boiling point 168°–170° C./0.3 mm Hg), 3-(3-(3-methoxyphenyl)-propyl)-aniline (boiling point 181°–182° C./0.4 mm Hg), 3-(3-(3-methylphenyl)-propyl)-aniline (boiling point 142°–145° C./0.01 mm Hg), 3-(3-(4-methylphenyl)-propyl)-aniline (boiling point 148°–150° C./0.1 mm Hg), 3-(3-(3-trifluoromethylphenyl)-propyl)-aniline (boiling point 142°–143° C./0.1 mm Hg), 3-(3-(4-fluorophenyl)-propyl)-aniline (boiling point 125°–217° C./0.1 mm Hg), 3-(3-(4-tert.-butylphenyl)-propyl)-aniline (boiling point 180°–185° C./0.4 mm Hg), 3-(3-(4-phenylphenyl)-propyl)-aniline (melting point 76°–77° C.), 3-(3-(4-ethylphenyl)-propyl)-aniline (boiling point 165°–168° C./0.2 mm Hg), 3-(3-(3-chlorophenyl)-propyl)-aniline (boiling point 153°–155° C./0.1 mm Hg), 3-(3-(3-hydroxyphenyl)-propyl)-aniline (melting point 59°–61° C.), 3-(3-(3,4-dimethoxyphenyl)-propyl)-aniline (boiling point 195° C./0.15 mm Hg), 3-(3-(4-methoxyphenyl)-propyl)-aniline (boiling point 176° C./0.1 mm Hg), 4-(3-phenylpropyl)-aniline (boiling point 156°–157° C./0.4 mm Hg), 3-(2-methyl-3-phenyl-propyl)-aniline (boiling point 152°–153° C./0.4 mm Hg), 3-(2-methyl-3-(4-fluorophenyl)-propyl)-aniline (boiling point 166°–172° C./0.4 mm Hg), 3-(4-methyl-5-phenyl-pentyl)-aniline (boiling point 177°–179° C./0.3 mm Hg), 4-(3-(4-methylphenyl)-propyl)-aniline (melting point 50°–53° C.), 3-(2-ethyl-3-phenylpropyl)-aniline (boiling point 154°–162° C./0.2 mm Hg) and 4-bromo-3-(3-phenylpropyl)-aniline (boiling point 159°–160° C./0.1 mm Hg).

EXAMPLE 1

8.14 g of tert.-butanol are added to a solution of 23.7 g of 3-(3-phenylpropyl)-phenyl isocyanate and 1 drop of triethylamine in 200 ml of absolute toluene. The mixture is left to stand for five days and the solvent is then dissolved off. 24.5 g of a white crystalline substance, having a melting point of 83°–85° C. and the following structural formula (active ingredient No. 1)

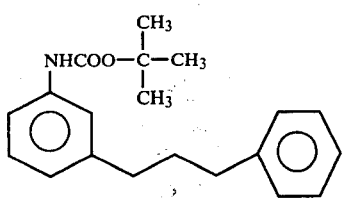

are obtained.

EXAMPLE 2

7.9 g of cyclopropanecarboxylic acid chloride are added dropwise, at 20° C., to a mixture of 15.8 g of 3-(3-phenylpropyl)-aniline, 8.5 g of $NaHCO_3$ and 200 ml of THF. The mixture is stirred overnight and is then filtered, the solvent is distilled off and the residue is stirred with petroleum ether. The product is filtered off and dried, giving 19.3 g of a compound which melts at 96°–99° C. and has the following structural formula (active ingredient No. 2):

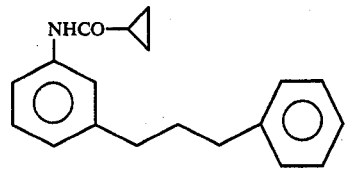

EXAMPLE 3

253 g of 1-phenyl-3-(3-nitrophenyl)-prop-2-en-1-one and 10 g of 10% strength palladium on animal charcoal, in a mixture of 2.5 liters of glacial acetic acid and 430 g of acetic anhydride, are hydrogenated at 65°–70° C., under a hydrogen pressure of 1.1 bar, until hydrogen is no longer absorbed. The mixture is filtered and the greater part of the acetic acid is then distilled off. The oil which remains is stirred into water and the solid obtained is filtered off.

239 g of a white crystalline substance, having a melting point of 71°–73° C. and the following structural formula (active ingredient No. 3)

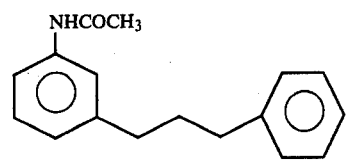

are obtained.

The following compounds may also be obtained by one of these processes.

| No. | R | Y | A | $(Z)_n$ | M.p. |
|---|---|---|---|---|---|
| 4 | $OCH_3$ | H | 3-$(CH_2)_3$ | H | 35–37° C. |
| 5 | $OC_2H_5$ | " | " | " | oil |
| 6 | O—iso$C_3H_7$ | " | " | " | oil |
| 7 | O—sec.$C_4H_9$ | " | " | " | 38–41° C. |
| 8 | O—$CH(CH_3)C\equiv CH$ | " | " | " | oil |
| 9 | $OCH_2CH=CH_2$ | " | " | " | oil |
| 10 | O—cycl.$C_6H_{11}$ | " | " | " | 49–51° C. |
| 11 | $OCH_2CH_2CN$ | " | " | " | oil |
| 12 | $OCH_2Cl$ | " | " | " | |
| 13 | $SCH_3$ | " | " | " | 77–79° C. |
| 14 | $SC_2H_5$ | " | " | " | |
| 15 | S—tert-$C_4H_9$ | " | " | " | 118–119° C. |

-continued

| No. | R | Y | A | (Z)$_n$ | M.p. |
|---|---|---|---|---|---|
| 16 | CCl$_3$ | " | " | " | |
| 17 | C$_2$H$_5$ | " | " | " | 53–55° C. |
| 18 | CHCl$_2$ | " | " | " | 99–103° C. |
| 19 | CH$_2$Cl | " | " | " | 67–69° C. |
| 20 | tert.C$_4$H$_9$ | " | " | " | 85–86° C. |
| 21 | CCl$_2$CH$_3$ | " | " | " | 73–75° C. |
| 22 | CH$_2$OCOCH$_3$ | " | " | " | 56–58° C. |
| 23 | C(CH$_3$)=CH$_2$ | " | " | " | |
| 24 | CH$_3$ | 4-Cl | " | " | |
| 25 | OCH$_3$ | " | " | " | |
| 26 | SCH$_3$ | " | " | " | |
| 27 | C$_2$H$_5$ | " | " | " | |
| 28 | OCH$_3$ | 4-CH$_3$ | " | " | |
| 29 | SCH$_3$ | " | " | 3-CH$_3$ | |
| 30 | C$_2$H$_5$ | " | " | 4-CH$_3$ | |
| 31 | OCH$_3$ | 4-OCH$_3$ | " | 3-CH$_3$ | |
| 32 | SCH$_3$ | " | " | 4-SCN | |
| 33 | C$_2$H$_5$ | " | " | 3-CN | |
| 34 | OCH$_3$ | H | " | 3-OCH$_3$ | 43–45° C. |
| 35 | OC$_2$H$_5$ | " | " | " | oil |
| 36 | SCH$_3$ | " | " | " | 76–78° C. |
| 37 | C$_2$H$_5$ | " | " | " | 59–61° C. |
| 38 | cycl.C$_3$H$_5$ | " | " | " | 60–62° C. |
| 39 | tert.C$_4$H$_9$ | " | " | " | 80–82° C. |
| 40 | SCH$_3$ | " | " | 4CH$_2$OCH$_3$ | |
| 41 | OCH$_3$ | " | " | 4cycl.C$_5$H$_9$ | |
| 42 | OCH$_3$ | " | " | 3-Br | |
| 43 | OCH$_3$ | " | " | 4CH$_2$—C$_6$H$_5$ | |
| 44 | C$_2$H$_5$ | " | " | 4-Br | |
| 45 | OCH$_3$ | " | " | 3O—isoC$_3$H$_7$ | |
| 46 | SCH$_3$ | " | " | " | |
| 47 | C$_2$H$_5$ | " | " | " | 89–91° C. |
| 48 | SCH$_3$ | " | " | 3OC$_2$H$_5$ | |
| 49 | C$_2$H$_5$ | " | " | " | |
| 50 | OCH$_3$ | " | " | 3OCHF$_2$ | |
| 51 | SCH$_3$ | " | " | " | |
| 52 | C$_2$H$_5$ | " | " | " | |
| 53 | C$_2$H$_5$ | " | " | 4SCH$_3$ | |
| 54 | SCH$_3$ | " | " | 4N(CH$_3$)$_2$ | |
| 55 | OCH$_3$ | H | 3-CH$_2$ | H | 63–64° C. |
| 56 | SCH$_3$ | " | " | " | 93–94° C. |
| 57 | SC$_2$H$_5$ | " | " | " | 65–66° C. |
| 58 | C$_2$H$_5$ | " | " | " | 67–69° C. |
| 59 | tert.C$_4$H$_9$ | " | " | " | |
| 60 | OCH$_3$ | " | 3-CH$_2$—CH$_2$ | " | 84–85° C. |
| 61 | SCH$_3$ | " | " | " | 106–108° C. |
| 62 | C$_2$H$_5$ | " | " | " | 117–120° C. |
| 63 | OCH$_3$ | " | 4-(CH$_2$)$_3$ | " | 76–78° C. |
| 64 | SCH$_3$ | " | " | " | 93–96° C. |
| 65 | C$_2$H$_5$ | " | " | " | 108–110° C. |
| 66 | OCH$_3$ | 3-Cl | " | " | |
| 67 | SCH$_3$ | " | " | " | |
| 68 | C$_2$H$_5$ | " | " | " | |
| 69 | OCH$_3$ | H | 3-(CH$_2$)$_3$ | 2-Cl | oil |
| 70 | SCH$_3$ | " | " | " | 72–74° C. |
| 71 | C$_2$H$_5$ | " | " | " | |
| 72 | OCH$_3$ | " | 3-(CH$_2$)$_3$ | 3-Cl | 44–46° C. |
| 73 | SCH$_3$ | " | " | " | 84–85° C. |
| 74 | C$_2$H$_5$ | " | " | " | 78–80° C. |
| 75 | OCH$_3$ | " | " | 4-Cl | 83–84° C. |
| 76 | SCH$_3$ | " | " | " | 129–131° C. |
| 77 | C$_2$H$_5$ | " | " | " | 92–93° C. |
| 78 | OCH$_3$ | " | " | 4-F | 73–75° C. |
| 79 | OC$_2$H$_5$ | " | " | " | |
| 80 | SCH$_3$ | " | " | " | 108–110° C. |
| 81 | C$_2$H$_5$ | " | " | " | 93–94° C. |
| 82 | OCH$_3$ | " | " | 4-OCH$_3$ | 56–58° C. |
| 83 | SCH$_3$ | " | " | " | 94–96° C. |
| 84 | C$_2$H$_5$ | " | " | " | |
| 85 | OCH$_3$ | " | " | 3-OH | 65–67° C. |
| 86 | SCH$_3$ | " | " | " | 89–91° C. |
| 87 | C$_2$H$_5$ | " | " | " | 68–71° C. |
| 88 | OCH$_3$ | " | " | 3,4(OCH$_3$)$_2$ | |
| 89 | OCH$_3$ | " | " | 2,3-(CH=CH—CH=CH)— | oil |
| 90 | SCH$_3$ | " | " | " | 96–97° C. |
| 91 | C$_2$H$_5$ | " | " | " | 92–94° C. |
| 92 | OCH$_3$ | " | " | 2,4(CH$_3$)$_2$ | |
| 93 | SCH$_3$ | " | " | " | |
| 94 | C$_2$H$_5$ | " | " | " | |
| 95 | OCH$_3$ | " | 3-(CH$_2$)$_4$ | H | 28–30° C. |
| 96 | SCH$_3$ | " | 3-(CH$_2$)$_5$ | " | |

-continued

| No. | R | Y | A | (Z)$_n$ | M.p. |
|---|---|---|---|---|---|
| 97 | OCH$_3$ | " | 3-CH$_2$CH(CH$_3$)CH$_2$ | " | 60–61° C. |
| 98 | SCH$_3$ | " | " | " | 85–87° C. |
| 99 | C$_2$H$_5$ | " | " | " | oil |
| 100 | OCH$_3$ | " | " | 4-F | |
| 101 | SCH$_3$ | " | " | " | |
| 102 | C$_2$H$_5$ | " | " | " | |
| 103 | OCH$_3$ | " | 3-CH$_2$CH(C$_2$H$_5$)CH$_2$ | H | oil |
| 104 | SCH$_3$ | " | " | " | oil |
| 105 | C$_2$H$_5$ | " | " | " | 48–50° C. |
| 106 | OCH$_3$ | " | 3-(CH$_2$)$_3$CH(CH$_3$)CH$_2$ | " | 43–44° C. |
| 107 | SCH$_3$ | " | " | " | 64–65° C. |
| 108 | C$_2$H$_5$ | " | " | " | 37–39° C. |
| 109 | OCH$_3$ | " | 3-(CH$_2$)$_3$ | 3-NHCOOCH$_3$ | |
| 110 | SCH$_3$ | " | " | 3-NHCOSCH$_3$ | |
| 111 | C$_2$H$_5$ | " | " | 3-NHCOC$_2$H$_5$ | |
| 112 | OCH$_3$ | " | " | 3-COOC$_2$H$_5$ | |
| 113 | OCH$_3$ | " | " | 2-OCH$_3$ | 54–56° C. |
| 114 | SCH$_3$ | " | " | " | 68–70° C. |
| 115 | C$_2$H$_5$ | " | " | " | 66–68° C. |
| 116 | OCH$_3$ | " | " | 3,4-Cl$_2$ | |
| 117 | SCH$_3$ | " | " | " | |
| 118 | C$_2$H$_5$ | " | " | " | 79–80° C. |
| 119 | OCH$_3$ | " | " | 2,6-Cl$_2$ | |
| 120 | SCH$_3$ | " | " | " | |
| 121 | C$_2$H$_5$ | " | " | " | |
| 122 | OCH$_3$ | " | " | 3-CF$_3$ | 75–76° C. |
| 123 | OC$_2$H$_5$ | " | " | " | |
| 124 | SCH$_3$ | " | " | " | 97–98° C. |
| 125 | C$_2$H$_5$ | " | " | " | 89–90° C. |
| 126 | cycl.C$_3$H$_5$ | " | " | " | |
| 127 | tert.C$_4$H$_9$ | " | " | " | |
| 128 | OCH$_3$ | " | " | 4C$_6$H$_5$ | 75–77° C. |
| 129 | SCH$_3$ | " | " | " | 102–104° C. |
| 130 | C$_2$H$_5$ | " | " | " | 94–96° C. |
| 131 | tert.C$_4$H$_9$ | " | " | " | |
| 132 | OCH$_3$ | " | " | 2-CH$_3$ | oil |
| 133 | SCH$_3$ | " | " | " | 56–57° C. |
| 134 | C$_2$H$_5$ | " | " | " | 70–72° C. |
| 135 | OCH$_3$ | " | " | 4-C$_2$H$_5$ | 80–82° C. |
| 136 | OC$_2$H$_5$ | " | " | " | |
| 137 | SCH$_3$ | " | " | " | 98–100° C. |
| 138 | OCH$_2$Cl | " | " | " | oil |
| 139 | C$_2$H$_5$ | " | " | " | 61–63° C. |
| 140 | CH$_2$OCH$_3$ | " | " | " | 53–55° C. |
| 141 | OCH$_3$ | " | " | 4-tert.C$_4$H$_9$ | 57–59° C. |
| 142 | SCH$_3$ | " | " | " | 71–72° C. |
| 143 | S—n-C$_3$H$_7$ | " | " | " | 47–50° C. |
| 144 | C$_2$H$_5$ | " | " | " | 75–76° C. |
| 145 | tert.C$_4$H$_9$ | " | " | " | 95–97° C. |
| 146 | C(CH$_3$)=CH$_2$ | " | " | " | |
| 147 | OCH$_3$ | " | " | 4-CH$_3$ | 72–74° C. |
| 148 | SCH$_3$ | " | " | " | 103–105° C. |
| 149 | C$_2$H$_5$ | " | " | " | 95–97° C. |
| 150 | OCH$_3$ | " | " | 2,5Cl$_2$ | |
| 151 | SCH$_3$ | " | " | " | |
| 152 | C$_2$H$_5$ | " | " | " | |
| 153 | OCH$_3$ | " | " | 2,4Cl$_2$ | |
| 154 | SCH$_3$ | " | " | " | |
| 155 | C$_2$H$_5$ | " | " | " | |
| 156 | OCH$_3$ | " | " | 3-CH$_3$ | 50–52° C. |
| 157 | OC$_2$H$_5$ | " | " | " | oil |
| 158 | SCH$_3$ | " | " | " | 81–83° C. |
| 159 | C$_2$H$_5$ | " | " | " | 58–60° C. |
| 160 | tert.C$_4$H$_9$ | " | " | " | 95–97° C. |
| 161 | sec.C$_5$H$_{11}$ | " | " | H | |
| 162 | ⊲CH$_3$ | " | " | " | |
| 163 | cycl.C$_6$H$_{11}$ | " | " | " | |
| 164 | tert.C$_4$H$_9$ | " | " | 4-F | 101–102° C. |
| 165 | cycl.C$_3$H$_5$ | " | " | " | 96–98° C. |
| 166 | tert.C$_4$H$_9$ | " | " | 4C$_2$H$_5$ | 85–87° C. |
| 167 | tert.C$_4$H$_9$ | " | 3-CH$_2$CH(CH$_3$)CH$_2$ | H | 94–96° C. |
| 168 | cycl.C$_3$H$_5$ | " | " | " | 73–75° C. |
| 169 | cycl.C$_3$H$_5$ | " | 3-(CH$_2$)$_3$ | 4C(CH$_3$)$_3$ | 119–121° C. |
| 170 | CH$_3$ | 4-Br | 3-(CH$_2$)$_3$ | H | 156–157° C. |
| 171 | OCH$_3$ | " | " | " | oil |
| 172 | SCH$_3$ | " | " | " | 97–100° C. |

-continued

| No. | R | Y | A | (Z)$_n$ | M.p. |
|---|---|---|---|---|---|
| 173 | C$_2$H$_5$ | " | " | " | 103–105° C. |
| 174 | OCH$_3$ | H | 4-(CH$_2$)$_3$ | 4CH$_3$ | 53–55° C. |
| 175 | SCH$_3$ | " | " | " | 99–100° C. |
| 176 | C$_2$H$_5$ | " | " | " | 94–96° C. |
| 177 | OCH$_3$ | " | 3-(CH$_2$)$_3$ | 3O—C$_6$H$_5$ | 72–74° C. |
| 178 | SCH$_3$ | " | " | " | 78–80° C. |
| 179 | C$_2$H$_5$ | " | " | " | 46–48° C. |
| 180 | OCH$_3$ | " | " | 3OCF$_2$CHF$_2$ | oil |
| 181 | SCH$_3$ | " | " | " | 67–69° C. |
| 182 | C$_2$H$_5$ | " | " | " | 73–75° C. |
| 183 | OCH$_3$ | " | " | 2,4,6(CH$_3$)$_3$ | |
| 184 | SCH$_3$ | " | " | " | |
| 185 | C$_2$H$_5$ | " | " | " | |
| 186 | SCH$_3$ | " | " | 4-OC$_2$H$_5$ | 95–97° C. |
| 187 | OCH$_3$ | " | " | " | 71–73° C. |
| 188 | C$_2$H$_5$ | " | " | " | 90–91° C. |
| 189 | SCH$_3$ | " | 4-(CH$_2$)$_3$ | 4-F | 98–101° C. |
| 190 | C$_2$H$_5$ | " | " | " | 98–101° C. |
| 191 | OCH$_3$ | " | 4-CH$_2$ | 4-phenyl | 133–136° C. |
| 192 | SCH$_3$ | " | " | " | 148–150° C. |
| 193 | C$_2$H$_5$ | " | " | " | 196–198° C. |
| 194 | Cyclopropyl | " | 3-(CH$_2$)$_3$ | 2-CH$_3$ | 99–101° C. |
| 195 | Cyclopropyl | " | " | 3-Cl | 88–89° C. |
| 196 | Cyclopropyl | " | 4-(CH$_2$)$_3$ | 4-CH$_3$ | 113–115° C. |
| 197 | CH$_2$Cl | " | " | H | 126–128° C. |
| 198 | SCH$_3$ | " | 4-(CH$_2$)$_4$ | H | 95–97 |
| 199 | C$_2$H$_5$ | " | 3-(CH$_2$)$_4$ | H | 50–52° C. |
| 200 | SCH$_3$ | " | 4-(CH$_2$)$_2$ | H | 120–122 |
| 201 | C$_2$H$_5$ | " | " | H | 108–110° C. |

Application may be effected for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used.

For the preparation of solutions, emulsions, pastes and oil dispersions to be sprayed direct, mineral oil fractions of medium to high boiling point, such as kerosene of diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably from 0.5 to 90, wt% of active ingredient.

The active ingredients are applied to the plants or soil for example by watering, scattering, dusting, spraying or atomizing, or by injecting or coating plants, or they are introduced into the irrigation water.

EXAMPLE I 90 parts by weight of compound 1 is mixed with 10 parts by weight of N-methyl-α-pyrrolidone. A mixture is obtained which is suitable for application in the form of very fine drops.

EXAMPLE II 20 parts by weight of compound 2 is dissolved in a mixture consisting of 90 parts by weight of xylene, 6 parts by weight of the adduct of 8 to 10 moles of ethylene oxide with 1 mole of oleic acid-N-monoethanolamide, 2 parts by weight of the calcium salt of dodecylbenzenesulfonic acid, and 2 parts by weight of the adduct of 40 moles of ethylene oxide with 1 mole of castor oil.

EXAMPLE III 20 parts by weight of compound 2 is dissolved in a mixture consisting of 60 parts by weight of cyclohexanone, 30 parts by weight of isobutanol, 5 parts by weight of the adduct of 7 moles of ethylene oxide with 1 mole of isooctylphenol, and 5 parts by weight of the adduct of 40 moles of ethylene oxide with 1 mole of castor oil.

EXAMPLE IV 20 parts by weight of compound 3 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide with 1 mole of castor oil.

EXAMPLE V 80 parts by weight of compound 1 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill.

EXAMPLE VI 5 parts by weight of compound 1 is intimately mixed with 95 parts by weight of particulate kaolin. A dust is obtained containing 5% by weight of the active ingredient.

EXAMPLE VII 30 parts by weight of compound 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE VIII 40 parts by weight of compound 1 is intimately mixed with 10 parts of the sodium salt of a phenolsulfonic acid-urea-formaldehyde condensate, 2 parts of silica gel and 48 parts of water to give a stable, aqueous dispersion.

EXAMPLE IX 20 parts of compound 1 is intimately mixed with 12 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or agents may be applied pre- or post-emergence. Preferably, the new active ingredients are applied after emergence of the unwanted plants, both to cropland and uncropped land.

If the crop plants tolerate the active ingredients less well, application techniques may be used in which the agents are sprayed from suitable equipment in such a manner that the leaves of sensitive crop plants are if possible not touched, and the agents reach the soil or the unwanted plants growing beneath the crop plants (post-directed, lay-by treatment).

Depending on the season and the growth stage of the plants, the application rates of active ingredient are from 0.1 to 15 kg/ha and more.

The influence of various representatives of the novel herbicidal aralkylaniline derivatives according to the invention on the growth of unwanted plants is demonstrated in greenhouse experiments.

The vessels employed were plastic flowerpots having a volume of 300 $cm^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate in this method was equivalent to 3.0 kg of active ingredient per hectare. After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the chemicals.

For the postemergence treatment, the plants were first grown in the vessels to a height of from 3 to 10 cm, depending on growth form, before being treated. For this treatment, plants were selected which had been sown in the vessels direct and grown there, or which had been grown separately as seedlings and transplanted to the vessels a few days before treatment. The application rates in this method varied from compound to compound: either 0.25, 0.5 or 1.0 kg of active ingredient per hectare. The prior art (German Laid-Open Application De-OS No. 2,855,699) compounds used for comparison purposes were N-(3-(2-phenylethoxy)-phenyl)-O-methylcarbamate (A) at 0.25 kg/ha, N-(3-(2-phenylethoxy)-phenyl)-O-ethylcarbamate (B) at 0.5 kg/ha, N-(3-(2-phenylethoxy)-phenyl)-propionamide (C) at 0.5 kg/ha, and N-(3-(2-(4-chlorophenyl)-ethoxy)-phenyl)-O-methylcarbamate (D) at 0.25 kg/ha. No cover was placed on the vessels.

The pots were set up in the greenhouse-species from warmer areas at from 20° to 30° C., and species from moderate climates at 15° to 25° C. The experiments were run for from 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The results obtained show that, on postemergence application, the novel compounds have a better herbicidal action than the comparative agents on a number of unwanted plants. In addition, some compounds according to the invention are better tolerated by certain crop plants. A herbicidal action is also observed on preemergence application.

In view of the good tolerance of the active ingredients and the many application methods possible, the agents according to the invention may be used in a large range of crops for removing unwanted plants. Application rates may vary from 0.1 to 15 kg/ha and more.

The following crop plants may be mentioned by way of example:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rape |
| *Brassica napus* var. *napobrassica* | |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora*, *Coffea liberica*) | coffee plants |
| *Cucumis melo* | melons |
| *Cucumis sativus* | cucumbers |
| *Cynodon dactylon* | Bermudagrass in turf and lawns |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum Gossypium herbaceum Gossypium vitifolium*) | cotton |
| *Helianthus annuus* | sunflowers |
| *Helianthus tuberosus* | |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicothiana tabacum* (*N. rustica*) | tobacco |
| *Olea europaea* | olive trees |
| *Oryza sativa* | rice |
| *Panicum miliaceum* | |
| *Phaseolus lunatus* | limabeans |
| *Phaseolus mungo* | mungbeans |
| *Phaseolus vulgaris* | snapbeans, green beans, dry beans |
| *Pennisetum glaucum* | |
| *Petroselinum crispum* | parsley |
| spp. *tuberosum* | |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Sesamum indicum* | sesame |

| Botanical name | Common name |
|---|---|
| *Solanum tuberosum* | Irish potatoes |
| *Sorghum bicolor* (*s. vulgare*) | sorghum |
| *Sorghum dochna* | |
| *Spinacia oleracea* | spinach |
| *Theobroma cacao* | cacao plants |
| *Trifolium pratense* | red clover |
| *Triticum aestivum* | wheat |
| *Vaccinium corymbosum* | blueberries |
| *Vaccinium vitis-idaea* | cranberries |
| *Vicia faba* | tick beans |
| *Vigna sinensis* (*V. unguiculata*) | cow peas |
| *Vitis vinifera* | grapes |
| *Zea mays* | Indian corn, sweet corn, maize |

To increase the spectrum of action and to achieve synergistic effects, the novel aralkylaniline derivatives may be mixed among themselves or mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc. A number of active ingredients which, when combined with the new compounds, give mixtures useful for widely varying applications are given below by way of example:

5-amino-4-chloro-2-phenyl-3(2H)-pyridazinone
5-amino-4-bromo-2-phenyl-3(2H)-pyridazinone
5-amino-4-chloro-2-cyclohexyl-3(2H)-pyridazinone
5-amino-4-bromo-2-cyclohexyl-3(2H)-pyridazinone
5-methylamino-4-chloro-2-(3-trifluoromethylphenyl)-3(2H)-pyridazinone
5-methylamino-4-chloro-2-(3-α,α,β,β-tetrafluoroethoxyphenyl)-3(2H)-pyridazinone
5-dimethylamino-4-chloro-2-phenyl-3(2H)-pyridazinone
4,5-dimethoxy-2-phenyl-3(2H)-pyridazinone
4,5-dimethoxy-2-cyclohexyl-3(2H)-pyridazinone
4,5-dimethoxy-2-(3-trifluoromethylphenyl)-3(2H)-pyridazinone
5-methoxy-4-chloro-2-(3-trifluoromethylphenyl)-3(2H)-pyridazinone
5-amino-4-bromo-2(3-methylphenyl)-3(2H)-pyridazinone
3-(1-methylethyl)-1H-2,1,3-benzothiadiazin-4(3H)-one-2,2-dioxide and salts
3-(1-methylethyl)-8-chloro-1H-2,1,3-benzothiadiazin-4(3H)-one-2,2-dioxide and salts
3-(1-methylethyl)-8-fluoro-1H-2,1,3-benzothiadiazin-4(3H)-one-2,2-dioxide and salts
3-(1-methylethyl)-8-methyl-1H-2,1,3-benzothiadiazin-4(3H)-one-2,2-dioxide and salts
1-methoxymethyl-3-(1-methylethyl)-2,1,3-benzothiadiazin-4(3H)-one-2,2-dioxide
1-methoxymethyl-8-chloro-3-(1-methylethyl)-2,1,3-benzothiadiazin-4(3H)-one-2,2-dioxide
1-methoxymethyl-8-fluoro-3-(1-methylethyl)-2,1,3-benzothiadiazin-4(3H)-one-2,2-dioxide
1-cyano-8-chloro-3-(1-methylethyl)-2,1,3-benzothiadiazin-4(3H)-one-2,2-dioxide
1-cyano-8-fluoro-3-(1-methylethyl)-2,1,3-benzothiadiazin-4(3H)-one-2,2-dioxide 1-cyano-8-methyl-3-(1-methylethyl)-2,1,3-benzothiadiazin-4(3H)-one-2,2-dioxide
1-cyano-3-(1-methylethyl)-2,1,3-benzothiadiazin-4(3H)-one-2,2-dioxide
1-azidomethyl-3-(1-methylethyl)-2,1,3-benzothiadiazin-4(3H)-one-2,2-dioxide
3-(1-methylethyl)-1H-pyridino-[3,2-e]-2,1,3-thiadiazin-(4)-one-2,2-dioxide
N-(1-ethylpropyl)-2,6-dinitro-3,4-dimethylaniline
N-(1-methylethyl)-N-ethyl-2,6-dinitro-4-trifluoromethylaniline
N-n-propyl-N-β-chloroethyl-2,6-dinitro-4-trifluoromethylaniline
N-n-propyl-N-cyclopropylmethyl-2,6-dinitro-4-trifluoromethylaniline
N-bis-(n-propyl)-2,6-dinitro-3-amino-4-trifluoromethylaniline
N-bis-(n-propyl)-2,6-dinitro-4-methylaniline
N-bis-(n-propyl)-2,6-dinitro-4-methylsulfonylaniline
N-bis-(n-propyl)-2,6-dinitro-4-aminosulfonylaniline
bis-(β-chloroethyl)-2,6-dinitro-4-methylaniline
N-ethyl-N-(2-methylallyl)-2,6-dinitro-4-trifluoromethylaniline
3,4-dichlorobenzyl N-methylcarbamate
2,6-di-tert.butyl-4-methylphenyl N-methylcarbamate
isopropyl N-phenylcarbamate
3-methoxyprop-2-yl N-3-fluorophenylcarbamate
isopropyl N-3-chlorophenylcarbamate
but-1-yn-3-yl N-3-chlorophenylcarbamate
4-chlorobut-2-yn-1-yl N-3-chlorophenylcarbamate
methyl N-3,4-dichlorophenylcarbamate
methyl N-(4-aminobenzenesulfonyl)-carbamate
O-(N-phenylcarbamoyl)-propanone oxime
N-ethyl-2-(phenylcarbamoyl)-oxypropionic acid amide
3'-N-isopropylcarbamoyloxypropionanilide
ethyl-N-(3-(N'-phenylcarbamoyloxy)-phenyl)-carbamate
methyl-N-(3-(N'-methyl-N'-phenylcarbamoyloxy)-phenyl)-carbamate
isopropyl-N-(3-(N'-ethyl-N'-phenylcarbamoyloxy)-phenyl)-carbamate
methyl-N-(3-(N'-3-methylphenylcarbamoyloxy)-phenyl)-carbamate
methyl-N-(3-(N'-4-fluorophenylcarbamoyloxy)-phenyl)-carbamate
methyl-N-(3-(N'-3-chloro-4-fluorophenylcarbamoyloxy)-phenyl)-carbamate
ethyl-N-[3-N'-(3-chloro-4-fluorophenylcarbamoyloxy)-phenyl]-carbamate
ethyl-N-[3-N'-(3,4-difluorophenylcarbamoyloxy)-phenyl]-carbamate
methyl-N-[3-(N'-3,4-difluorophenylcarbamoyloxy)-phenyl]-carbamate
methyl N-3-(4'-fluorophenoxycarbonylamino)-phenyl-carbamate
ethyl N-3-(2'-methylphenoxycarbonylamino)-phenyl-carbamate
methyl N-3-(4'-fluorophenoxycarbonylamino)-phenyl-thiolcarbamate
methyl N-3-(2',4',5'-trimethylphenoxycarbonylamino)-phenylthiolcarbamate
methyl N-3-(phenoxycarbonylamino)-phenylthiolcarbamate
p-chlorobenzyl N,N-diethylthiolcarbamate
ethyl N,N-di-n-propylthiolcarbamate
n-propyl N,N-di-n-propylthiolcarbamate
2,3-dichloroallyl N,N-diisopropylthiolcarbamate
2,3,3-trichloroallyl N,N-diisopropylthiolcarbamate
3-methyl-5-isoxazolylmethyl N,N-diisopropylthiolcarbamate
3-ethyl-5-isoxazolylmethyl N,N-diisopropylthiolcarbamate
ethyl N,N-di-sec.-butylthiolcarbamate
benzyl N,N-di-sec.-butylthiolcarbamate
ethyl N-ethyl-N-cyclohexylthiolcarbamate
ethyl N-ethyl-N-bicyclo-[2.1.1]-heptylthiolcarbamate
S-(2,3-dichloroallyl)-(2,2,4-trimethylazetidine)-1-carbothiolate
S-(2,3,3-trichloroallyl)-(2,2,4-trimethylazetidine)-1-carbothiolate
S-ethylhexahydro-1-H-azepine-1-carbothiolate
S-benzyl-(3-methylhexahydro-1H-azepine-1)-carbothiolate
S-benzyl-(2,3-dimethylhexahydro-1-H-azepine-1)-carbothiolate
S-ethyl-(3-methylhexahydro-1-H-azepine-1)-carbothiolate
n-propyl N-ethyl-N-n-butylthiolcarbamate
2-chloroallyl N,N-dimethyldithiocarbamate
N-methyldithiocarbamic acid, sodium salt
trichloroacetic acid, sodium salt
α,α-dichloropropionic acid, sodium salt
α,α-dichlorobutyric acid, sodium salt
α,α-β,β-tetrafluoropropionic acid, sodium salt
α-methyl-α,β-dichloropropionic acid, sodium salt
methyl α-chloro-β-(4-chlorophenyl)-propionate
methyl α,β-dichloro-β-phenylpropionate
benzamido oxyacetic acid
2,3,5-triiodobenzoic acid (salts, esters, amides)
2,3,6-trichlorobenzoic acid (salts, esters, amides)
2,3,5,6-tetrachlorobenzoic acid (salts, esters, amides)
2-methoxy-3,6-dichlorobenzoic acid (salts, esters, amides)
2-methoxy-3,5,6-trichlorobenzoic acid (salts, esters, amides)
3-amino-2,5,6-trichlorobenzoic acid (salts, esters, amides)
O,S-dimethyltetrachlorothioterephthalate
dimethyl-2,3,5,6-tetrachloroterephthalate
disodium 3,6-endoxohexahydrophthalate
4-amino-3,5,6-trichloropicolinic acid (salts)
ethyl 2-cyano-3-(N-methyl-N-phenyl)-aminoacrylate
isobutyl 2-[4-(4'-chlorophenoxy)-phenoxy]-propionate
methyl 2-[4-(2',4'-dichlorophenoxy)-phenoxy]-propionate
methyl 2-[4-(4'-trifluoromethylphenoxy)-phenoxy]-propionate
2-[4-(2'-chloro-4'-trifluorophenoxy)-phenoxy]-propionic acid, sodium salt
2-[4-(3',5'-dichloropyridyl-2-oxy)-phenoxy]-propionic acid, sodium salt
ethyl 2-(N-benzoyl-3,4-dichlorophenylamino)-propionate
methyl 2-(N-benzoyl-3-chloro-4-fluorophenylamino)-propionate
isopropyl 2-(N-benzoyl-3-chloro-4-fluorophenylamino)-propionate
2-chloro-4-ethylamino-6-isopropylamino-1,3,5-triazine
2-chloro-4-ethylamino-6-(amino-2'-propionitrile)-1,3,5-triazine
2-chloro-4-ethylamino-6-(2-methoxypropyl)-2-amino-1,3,5-triazine
2-chloro-4-ethylamino-6-butyn-1-yl-2-amino-1,3,5-triazine
2-chloro-4,6-bisethylamino-1,3,5-triazine 2-chloro-4,6-bisisopropylamino-1,3,5-triazine
2-chloro-4-isopropylamino-6-cyclopropylamino-1,3,5-triazine
2-azido-4-methylamino-6-isopropylamino-1,3,5-triazine
2-methylthio-4-ethylamino-6-isopropylamino-1,3,5-triazine
2-methylthio-4-ethylamino-6-tert.butylamino-1,3,5-triazine
2-methylthio-4,6-bisethylamino-1,3,5-triazine
2-methylthio-4,6-bisisopropylamino-1,3,5-triazine
2-methoxy-4-ethylamino-6-isopropylamino-1,3,5-triazine
2-methoxy-4,6-bisethylamino-1,3,5-triazine
2-methoxy-4,6-bisisopropylamino-1,3,5-triazine
4-amino-6-tert.butyl-3-methylthio-4,5-dihydro-1,2,4-triazin-5-one
4-amino-6-phenyl-3-methyl-4,5-dihydro-1,2,4-triazin-5-one
4-isobutylidenamino-6-tert.butyl-3-methylthio-4,5-dihydro-1,2,4-triazin-5-one
1-methyl-3-cyclohexyl-6-dimethylamino-1,3,5-triazin-2,4-dione
3-tert.butyl-5-chloro-6-methyluracil
3-tert.butyl-5-bromo-6-methyluracil
3-isopropyl-5-bromo-6-methyluracil
3-sec.butyl-5-bromo-6-methyluracil
3-(2-tetrahydropyranyl)-5-chloro-6-methyluracil
3-(2-tetrahydropyranyl)-5,6-trimethyleneuracil
3-cyclohexyl-5,6-trimethyleneuracil
2-methyl-4-(3'-trifluoromethylphenyl)-tetrahydro-1,2,4-oxadiazine-3,5-dione
2-methyl-4-(4'-fluorophenyl)-tetrahydro-1,2,4-oxadiazine-3,5-dione
3-amino-1,2,4-triazole
1-allyloxy-1-(4-bromophenyl)-2-[1',2',4'-triazolyl-(1')]-ethane (salts)
1-(4-chlorophenoxy)-3,3-dimethyl-1-(1H-1,2,3-triazol-1-yl)-butan-2-one
N,N-diallylchloroacetamide
N-isopropyl-2-chloroacetanilide
N-(but-1-yn-3-yl)-2-chloroacetanilide
2-methyl-6-ethyl-N-propargyl-2-chloroacetanilide
2-methyl-6-ethyl-N-ethoxymethyl-2-chloroacetanilide
2-methyl-6-ethyl-N-(2-methoxy-1-methylethyl)-2-chloroacetanilide
2-methyl-6-ethyl-N-(isopropoxycarbonylethyl)-2-chloroacetanilide
2-methyl-6-ethyl-N-(4-methoxypyrazol-1-yl-methyl)-2-chloro-acetanilide
2-methyl-6-ethyl-N-(pyrazol-1-yl-methyl)-2-chloroacetanilide
2,6-dimethyl-N-(pyrazon-1-yl-methyl)-2-chloroacetanilide
2,6-dimethyl-N-(4-methylpyrazol-1-yl-methyl)-2-chloro-acetanilide
2,6-dimethyl-N-(1,2,4-triazol-1-yl-methyl)-2-chloroacetanilide
2,6-dimethyl-N-(3,5-dimethylpyrazol-1-yl-methyl)-2-chloroacetanilide
2,6-dimethyl-N-(1,3-dioxolan-2-yl-methyl)-2-chloroacetanilide
2,6-dimethyl-N-(2-methoxyethyl)-2-chloroacetanilide
2,6-dimethyl-N-isobutoxymethyl-2-chloroacetanilide
2,6-diethyl-N-methoxymethyl-2-chloroacetanilide
2,6-diethyl-N-n-butoxymethyl-2-chloroacetanilide
2,6-diethyl-N-ethoxycarbonylmethyl-2-chloroacetanilide
2,3,6-trimethyl-N-(pyrazol-1-yl-methyl)-2-chloroacetanilide
2,3-dimethyl-N-isopropyl-2-chloroacetanilide
2,6-diethyl-N-(propoxyethyl)-2-chloroacetanilide
2-(2-methyl-4-chlorophenoxy-N-methoxyacetamide
2-( -naphthoxy)-N,N-diethylpropionamide
2,2-diphenyl-N,N-dimethylacetamide
α-(3,4,5-tribromopyrazol-1-yl)-N,N-dimethylpropionamide
N-(1,1-dimethylpropynyl)-3,5-dichlorobenzamide
N-1-naphthylphthalamic acid
propionic acid 3,4-dichloroanilide
cyclopropanecarboxylic acid 3,4-dichloroanilide
methacrylic acid 3,4-dichloroanilide
2-methylpentanecarboxylic acid 3,4-dichloroanilide
5-acetamido-2,4-dimethyltrifluoromethanesulfone anilide
5-acetamido-4-methyltrifluoromethanesulfone anilide
2-propionylamino-4-methyl-5-chlorothiazole
O-(methylsulfonyl)-glycolic acid N-ethoxymethyl-2,6-dimethylanilide
O-(methylaminosulfonyl)-glycolic acid N-isopropylanilide
O-(isopropylaminosulfonyl)-glycolic acid N-but-1-yn-3-yl-anilide
O-(methylaminosulfonyl)-glycolic acid hexamethyleneamide
2,6-dichlorothiobenzamide
2,6-dichlorobenzonitrile
3,5-dibromo-4-hydroxybenzonitrile (salts)
3,5-diiodo-4-hydroxybenzonitrile (salts)
3,5-dibromo-4-hydroxy-O-2,4-dinitrophenylbenzaldoxime (salts)
3,5-dibromo-4-hydroxy-O-2-cyano-4-nitrophenylbenzaldoxime (salts)
pentachlorophenol, sodium salt
2,4-dichlorophenyl-4'-nitrophenyl ether
2,4,6-trichlorophenyl-4'-nitrophenyl ether
2-fluoro-4,6-dichlorophenyl-4'-nitrophenyl ether
2-chloro-4-trifluoromethylphenyl-4'-nitrophenyl ether
2,4'-dinitro-4-trifluoromethyl-diphenyl ether
2,4-dichlorophenyl-3'-methoxy-4'-nitro-phenyl ether
2-chloro-4-trifluoromethylphenyl-3'-ethoxy-4'-nitrophenyl ether
2-chloro-4-trifluoromethylphenyl-3'-carboxy-4'-nitrophenyl
ether (salts)
2,4-dichlorophenyl-3'-methoxycarbonyl-4'-nitro-phenyl ether
2-(3,4-dichlorophenyl)-4-methyl-1,2,4-oxadiazolidine-3,5-dione
2-(3-tert.butylcarbamoyloxyphenyl)-4-methyl-1,2,4-oxadiazolidine-3,5-dione
2-(3-isopropylcarbamoyloxyphenyl)-4-methyl-1,2,4-oxadiazolidine-3,5-dione
2-phenyl-3,1-benzoxazinone-(4)
(4-bromophenyl)-3,4,5,9,10-pentaazatetracyclo-[5,4,1,0$^{2,6}$,0,$^{8,11}$]-dodeca-3,9-diene
2-ethoxy-2,3-dihydro-3,3-dimethyl-5-benzofuranylmethane sulfonate
2-ethoxy-2,3-dihydro-3,3-dimethyl-5-benzofuranyl-dimethylaminosulfate
2-ethoxy-2,3-dihydro-3,3-dimethyl-5-benzofuranyl-(N-methyl-N-acetyl)-aminosulfonate
3,4-dichloro-1,2-benzisothiazole
N-4-chlorophenyl-allylsuccinimide
2-methyl-4,6-dinitrophenol (salts, esters)
2-sec.butyl-4,6-dinitrophenol (salts, esters)

2-sec.butyl-4,6-dinitrophenol acetate
2-tert.butyl-4,6-dinitrophenol acetate
2-tert.butyl-4,6-dinitrophenol (salts)
2-tert.butyl-5-methyl-4,6-dinitrophenol (salts)
2-tert.butyl-5-methyl-4,6-dinitrophenol acetate
2-sec.amyl-4,6-dinitrophenol (salts, esters)
1-(α,α-dimethylbenzyl)-3-(4-methylphenyl)-urea
1-phenyl-3-(2-methylcyclohexyl)-urea
1-phenyl-1-benzoyl-3,3-dimethylurea
1-(4-chlorophenyl)-1-benzoyl-3,3-dimethylurea
1-(4-chlorophenyl)-3,3-dimethylurea
1-(4-chlorophenyl)-3-methyl-3-but-1-yn-3-yl-urea
1-(3,4-dichlorophenyl)-3,3-dimethylurea
1-(3,4-dichlorophenyl)-1-benzoyl-3,3-dimethylurea
1-(3,4-dichlorophenyl)-3-methyl-3-n.butylurea
1-(4-isopropylphenyl)-3,3-dimethylurea
1-(3-trifluoromethylphenyl)-3,3-dimethylurea
1-(α,α,β,β-tetrafluoroethoxyphenyl)-3,3-dimethylurea
1-(3-tert.butylcarbamoyloxyphenyl)-3,3-dimethylurea
1-(3-chloro-4-methylphenyl)-3,3-dimethylurea
1-(3-chloro-4-methoxyphenyl)-3,3-dimethylurea
1-(3,5-dichloro-4-methoxyphenyl)-3,3-dimethylurea
1-[4-(4'-chlorophenoxy)-phenyl]-3,3-dimethylurea
1-[4-(4'-methoxyphenoxy)-phenyl]-3,3-dimethylurea
1-cyclooctyl-3,3-dimethylurea
1-(hexahydro-4,7-methanoindan-5-yl)-3,3-dimethylurea
1-[1- or 2-(3a,4,5,7,7a-hexahydro)-4,7-methanoindanyl]-3,3-dimethylurea
1-(4-fluorophenyl)-3-carboxymethoxy-3-methylurea
1-phenyl-3-methyl-3-methoxyurea
1-(4-chlorophenyl)-3-methyl-3-methoxyurea
1-(4-bromophenyl)-3-methyl-3-methoxyurea
1-(3,4-dichlorophenyl)-3-methyl-3-methoxyurea
1-(3-chloro-4-bromophenyl)-3-methyl-3-methoxyurea
1-(3-chloro-4-isopropylphenyl)-3-methyl-3-methoxyurea
1-(3-chloro-4-methoxyphenyl)-3-methyl-3-methoxyurea
1-(3-tert.butylphenyl)-3-methyl-3-methoxyurea
1-(2-benzthiazolyl)-1,3-dimethylurea
1-(2-benzthiazolyl)-3-methylurea
1-(5-trifluoromethyl-1,3,4-thiadiazolyl)-1,3-dimethylurea
imidazolidin-2-one-1-carboxylic acid isobutylamide
1,2-dimethyl-3,5-diphenylpyrazolium-methylsulfate
1,2,4-trimethyl-3,5-diphenylpyrazolium-methylsulfate
1,2-dimethyl-4-bromo-3,5-diphenylpyrazolium-methylsulfate
1,3-dimethyl-4-(3,4-dichlorobenzoyl)-5-(4-methylphenylsulfonyloxy)-pyrazole
2,3,5-trichloropyridinol-(4)
1-methyl-3-phenyl-5-(3'-trifluoromethylphenyl)-pyridone-(4)
1-methyl-4-phenylpyridinium chloride
1,1-dimethylpyridinium chloride
3-phenyl-4-hydroxy-6-chloropyridazine
1,1'-dimethyl-4,4'-dipyridylium-di(methylsulfate)
1,1'-di-(3,5-dimethylmorpholine-carbonylmethyl)-4,4'-dipyridylium dichloride
1,1'-ethylene-2,2'-dipyridylium dibromide
3-[1-(N-ethoxyamino)-propylidene]-6-ethyl-3,4-dihydro-2H-pyran-2,4-dione
3-[1-(N-allyloxyamino)-propylidene]-6-ethyl-3,4-dihydro-2H-pyran-2,4-dione
2-[1-(N-allyloxyamino)-propylidene]-5,5-dimethylcyclohexane-1,3-dione (salts)
2-[1-(N-allyloxyamino-butylidene]-5,5-dimethylcyclohexane-1,3-dione (salts)
2-[1-(N-allyloxyamino-butylidene]-5,5-dimethyl-4-methoxycarbonyl-cyclohexane-1,3-dione (salts)
2-chlorophenoxyacetic acid (salts, esters, amides)
4-chlorophenoxyacetic acid (salts, esters, amides)
2,4-dichlorophenoxyacetic acid (salts, esters, amides)
2,4,5-trichlorophenoxyacetic acid (salts, esters, amides)
2-methyl-4-chlorophenoxyacetic acid (salts, esters, amides)
3,5,6-trichloro-2-pyridinyl-oxyacetic acid (salts, esters, amides)
methyl α-naphthoxyacetate
2-(2-methylphenoxy)-propionic acid (salts, esters, amides)
2-(4-chlorophenoxy)-propionic acid (salts, esters, amides)
2-(2,4-dichlorophenoxy)-propionic acid (salts, esters, amides)
2-(2,4,5-trichlorophenoxy)-propionic acid (salts, esters, amides)
2-(2-methyl-4-chlorophenoxy)-propionic acid (salts, esters, amides)
4-(2,4-dichlorophenoxy)-butyric acid (salts, esters, amides)
4-(2-methyl-4-chlorophenoxy)-butyric acid (salts, esters, amides)
cyclohexyl-3-(2,4-dichlorophenoxy)-acrylate
9-hydroxyfluorenecarboxylic acid-(9) (salts, esters)
2,3,6-trichlorophenylacetic acid (salts, esters)
4-chloro-2-oxobenzothiazolin-3-yl-acetic acid (salts, esters)
gibelleric acid (salts)
disodium methylarsonate
monosodium salt of methylarsonic acid
N-phosphonomethyl-glycine (salts)
N,N-bis-(phosphonomethyl)-glycine (salts)
2-chloroethyl 2-chloroethanephosphonate
ammonium-ethyl-carbamoyl-phosphonate
di-n-butyl-1-n-butylamino-cyclohexyl-phosphonate trithiobutylphosphite
O,O-diisopropyl-5-(2-benzosulfonylaminoethyl)-phosphorodithionate
2,3-dihydro-5,6-dimethyl-1,4-dithiin-1,1,4,4-tetraoxide
5-tert.butyl-3-(2,4-dichloro-5-isopropoxyphenyl)-1,3,4-oxadiazolone-(2)
4,5-dichloro-2-trifluoromethylbenzimidazole (salts)
1,2,3,6-tetrahydropyridazine-3,6-dione (salts)
succinic acid mono-N-dimethylhydrazide (salts)
(2-chloroethyl)-trimethylammonium chloride
(2-methyl-4-phenylsulfonyl)-trifluoromethanesulfone anilide
1,1-dimethyl-4,6-diisopropyl-5-indanyl ethyl ketone
sodium chlorate
ammonium thiocyanate
calcium cyanamide
2-chloro-4-trifluoromethyl-3'-ethoxycarbonyl-4'-nitrophenyl ether
1-(4-benzyloxyphenyl)-3-methyl-3-methoxyurea
2-[1-(2,5-dimethylphenyl)-ethylsulfonyl]-pyridine-N-oxide
1-acetyl-3-anilino-4-methoxycarbonyl-5-methylpyrazole
3-anilino-4-methoxycarbonyl-5-methylpyrazole
3-tert.butylamino-4-methoxycarbonyl-5-methylpyrazole
N-benzyl-N-isopropyl-trimethylacetamide
methyl 2-[4-(4'-chlorophenoxymethyl)-phenoxy]-propionate ethyl 2-[4-(5'-bromopyridyl-2-oxy)-phenoxy]-propionate
ethyl 2-[4-(5'-iodopyridyl-2-oxy)-phenoxy]-propionate
n-butyl 2-[4-(5'-iodopyridyl-2-oxy)-phenoxy]-propionate
2-chloro-4-trifluoromethylphenyl-3'-(2-fluoroethoxy)-4'-nitro-phenyl ether
2-chloro-4-trifluoromethylphenyl-3-(ethoxycarbonyl)-methylthio-4-nitrophenyl ether
2,4,6-trichlorophenyl-3-(ethoxycarbonyl)-methylthio-4-nitro-phenyl ether
2-[1-(N-ethoxamino)-butylidene]-5-(2-ethylthiopropyl)-3-hydroxy-cyclohex-2-en-1-one (salts)
2-[1-(N-ethoxamino)-butylidene]-5-(2-phenylthiopropyl)-3-hydroxy-cyclohex-2-en-1-one (salts)
ethyl 4-[4-(4'-trifluoromethyl)-phenoxy]-pentene-2-carboxylate
2-chloro-4-trifluoromethyl-3'-methoxycarbonyl-4'-nitrophenyl ether
2,4-dichlorophenyl-3'-carboxy-4'-nitrophenyl ether (salts)
4,5-dimethoxy-2-(3-α,α,β-trifluoro-β-bromoethoxyphenyl)-3-(2H)-pyridazinone
2,4-dichlorophenyl-3'-ethoxy-ethoxy-ethoxy-4'-nitrophenyl ether
2,3-dihydro-3,3-dimethyl-5-benzofuranyl-ethane sulfonate
N-[4-methoxy-6-methyl-1,3,5-triazin-2-yl-aminocarbonyl]-2-chlorobenzene sulfonamide
1(3-chloro-4-ethoxyphenyl)-3,3-dimethylurea
ethyl 2-methyl-4-chlorophenoxy-thioacetate
2-chloro-3,5-diiodo-4-acetoxy-pyridine.

It may also be useful to apply the mixtures according to the invention, either alone or in combination with other herbicides, in admixture with other crop protection agents, e.g., agents for combating pests or phytopathogenic fungi or bacteria. The compounds may also be mixed with solutions of mineral matters used to remedy nutritional or trace element deficiencies. Nonphytotoxic oils and oil concentrates may be added.

In investigations into the selective herbicidal action on postemergence treatment in the greenhouse at a rate of 0.25 kg of active ingredient per hectare, new compounds nos. 4 and 13 have a better action than prior art compound A.

New compound no. 148—also at 0.25 kg of active ingredient per hectare and postemergence treatment in the greenhouse—has a better herbicidal action than prior art compound D, and is also better tolerated.

In investigations into the selective herbicidal action on postemergence treatment in the greenhouse at a rate of 0.5 kg of active ingredient per hectare, new compounds nos. 17, 149 and 77 have a better action than prior art compound C.

New compound no. 5, also used for selective weed control on postemergence treatment in the greenhouse at a rate of 0.5 kg of active ingredient per hectare, has a better selective herbicidal action than prior art compound B.

In investigations into the herbicidal action on preemergence treatment in the greenhouse at a rate of 3.0 kg of active ingredient per hectare, some of new compounds nos. 1, 2, 4, 7, 20, 55, 58, 78, 81, 99, 129, 142, 144, 147, 157 and 159 have a very good action.

In investigations into the selective herbicidal action on postemergence application in the greenhouse at a rate of 0.25 kg of active ingredient per hectare, new compounds nos. 114, 124 and 98 exhibited a good herbicidal action.

In investigations into the selective herbicidal action on postemergence application in the greenhouse at a rate of 0.25 kg of active ingredient per hectare, new compound no. 87 exhibited a good herbicidal action.

In investigations into the selective herbicidal action on postemergence application in the greenhouse at a rate of 0.25 kg of active ingredient per hectare, new compound no. 187 exhibited a good herbicidal action.

In investigations into the selective herbicidal action on postemergence application in the greenhouse at a rate of 0.25 kg of active ingredient per hectare, new compound no. 147 exhibited a good herbicidal action.

In investigations into the selective herbicidal action on postemergence application in the greenhouse at a rate of 0.25 kg of active ingredient per hectare, new compounds nos. 37 and 38 exhibited a good herbicidal action.

We claim:

1. An aralkylaniline derivative of the formula

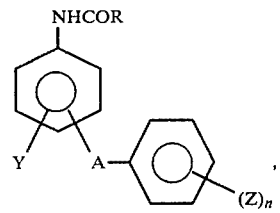

where R is alkoxy, cycloalkoxy, alkenyloxy, alkynyloxy, cyanoalkoxy, haloalkoxy, alkylthio, alkenylthio or alkynylthio or unsubstituted or halogen-, or cyano-substituted ethyl, isopropyl, n-propyl, n-butyl, sec-butyl, tert-butyl, isobutyl, sec-pentyl, cycloalkyl, alkenyl or alkynyl, Y is hydrogen, alkyl, halogen, alkoxy or haloalkyl, A is unsubstituted or alkyl-substituted alkylene which is attached at the 3- or 4-position of the phenyl radical, Z is hydrogen, alkyl, haloalkyl, alkoxyalkyl, cycloalkyl, aralkyl, aryl, aryloxy, halogen, a C$_4$H$_4$-chain which is fused to the benzene radical to form an unsubstituted or substituted naphthyl radical, alkoxy, haloalkoxy, alkylthio, thiocyanato, cyano,

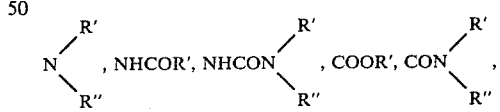

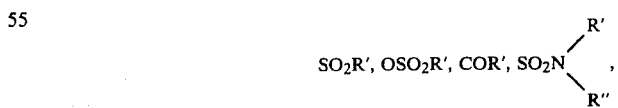

R' and R" each, independently of one another, being hydrogen, alkyl, alkoxy, alkylthio, cycloalkyl or unsubstituted or alkyl-, halogen- or alkoxy-substituted phenyl, and n is an integer from 1 to 4.

2. A process for combating the growth of unwanted plants, wherein the plants or the soil are treated with an effective herbicidal amount of an aralkylaniline derivative of the formula

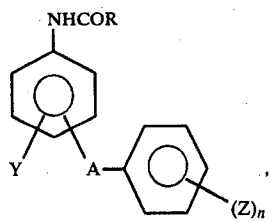

where R is alkoxy, cycloalkoxy, alkenyloxy, alkynyloxy, cyanoalkoxy, haloalkoxy, alkylthio, alkenylthio or alkynylthio or unsubstituted or halogen-, alkoxy-, alkoxycarbonyl- or cyano-substituted alkyl, cycloalkyl, alkenyl or alkynyl, Y is hydrogen, alkyl, halogen, alkoxy or haloalkyl, A is unsubstituted or alkyl-substituted alkylene which is attached at the 3- or 4-position of the phenyl radical, Z is hydrogen, alkyl, haloalkyl, alkoxyalkyl, cycloalkyl, aralkyl, aryl, aryloxy, halogen, a $C_4H_4$-chain which is fused to the benzene radical to form an unsubstituted or substituted naphthyl radical, alkoxy, haloalkoxy, alkylthio, thiocyanato, cyano,

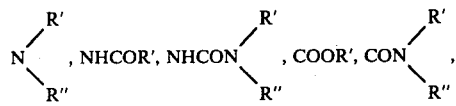

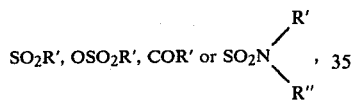

R' and R'' each, independently of one another, being hydrogen, alkyl, alkoxy, alkylthio, cycloalkyl or unsubstituted or alkyl-, halogen- or alkoxy-substituted phenyl, and n is an integer from 1 to 4.

3. A herbicidal composition comprising a carrier and/or diluent and from 0.1 to 95% by weight of a compound of the formula

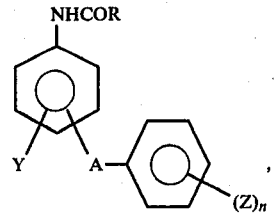

where R is alkoxy, cycloalkoxy, alkenyloxy, alkynyloxy, cyanoalkoxy, haloalkoxy, alkylthio, alkenylthio or alkynylthio or unsubstituted or halogen-, alkoxy-, alkoxycarbonyl- or cyano-substituted alkyl, cycloalkyl, alkenyl or alkynyl, Y is hydrogen, alkyl, halogen, alkoxy or haloalkyl, A is unsubstituted or alkyl-substituted allkylene which is attached at the 3- or 4-position of the phenyl radical, Z is hydrogen, alkyl, haloalkyl, alkoxyalkyl, cycloalkyl, aralkyl, aryl, aryloxy, halogen, a $C_4H_4$-chain which is fused to the benzene radical to form an unsubstituted or substituted naphthyl radical, alkoxy, haloalkoxy, alkylthio, thiocyanato, cyano,

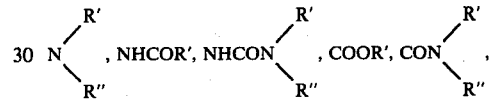

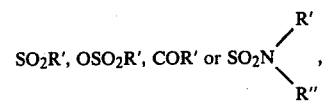

R' and R'' each, independently of one another, being hydrogen, alkyl, alkoxy, alkylthio, cycloalkyl or unsubstituted or alkyl-, halogen- or alkoxy-substituted phenyl, and n is an integer from 1 to 4.

* * * * *